United States Patent
Biemans et al.

(10) Patent No.: US 10,669,318 B2
(45) Date of Patent: *Jun. 2, 2020

(54) CONJUGATION PROCESS

(75) Inventors: Ralph Leon Biemans, Rixensart (BE); Pierre Duvivier, Rixensart (BE); Ollivier Francis Nicolas Gavard, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 455 days.

This patent is subject to a terminal disclaimer.

(21) Appl. No.: 14/002,411

(22) PCT Filed: Mar. 5, 2012

(86) PCT No.: PCT/EP2012/053715
§ 371 (c)(1),
(2), (4) Date: Aug. 30, 2013

(87) PCT Pub. No.: WO2012/119972
PCT Pub. Date: Sep. 13, 2012

(65) Prior Publication Data
US 2013/0344103 A1    Dec. 26, 2013

(30) Foreign Application Priority Data
Mar. 7, 2011   (GB) .................................. 1103836.1

(51) Int. Cl.
| | | |
|---|---|---|
| *A61K 39/385* | (2006.01) | |
| *C07K 16/00* | (2006.01) | |
| *C12P 21/08* | (2006.01) | |
| *C07K 14/34* | (2006.01) | |
| *A61K 39/02* | (2006.01) | |
| *A61K 39/09* | (2006.01) | |
| *A61K 39/102* | (2006.01) | |
| *A61K 47/64* | (2017.01) | |
| *A61K 39/095* | (2006.01) | |
| *A61K 39/00* | (2006.01) | |
| *A61K 47/68* | (2017.01) | |

(52) U.S. Cl.
CPC .............. *C07K 14/34* (2013.01); *A61K 39/02* (2013.01); *A61K 39/092* (2013.01); *A61K 39/102* (2013.01); *A61K 47/646* (2017.08); *A61K 47/6415* (2017.08); *A61K 39/095* (2013.01); *A61K 47/6889* (2017.08); *A61K 2039/6037* (2013.01); *A61K 2039/627* (2013.01); *Y02A 50/484* (2018.01)

(58) Field of Classification Search
CPC ........ A61K 47/4833; A61K 2039/6037; A61K 47/48261; A61K 39/092; A61K 2300/00; A61K 2039/62; A61K 2039/627; A61K 39/02; A61K 39/102; A61K 47/4823; A61K 47/48284; A61K 39/385; A61K 2039/555; A61K 2039/55522; A61K 2039/55544
See application file for complete search history.

(56) References Cited

U.S. PATENT DOCUMENTS

| | | |
|---|---|---|
| 4,673,574 A | 6/1987 | Anderson |
| 6,340,461 B1 * | 1/2002 | Terman ..................... 424/193.1 |
| 8,753,645 B2 * | 6/2014 | Biemans et al. ......... 424/197.11 |
| 2007/0184071 A1 * | 8/2007 | Hausdorff ............ A61K 39/092 424/244.1 |
| 2009/0043077 A1 * | 2/2009 | Berti ...................... A61K 39/09 530/363 |
| 2014/0186390 A1 * | 7/2014 | Biemans et al. ......... 424/197.11 |

FOREIGN PATENT DOCUMENTS

| | | |
|---|---|---|
| WO | 2007071707 | 6/2007 |
| WO | 2008/079732 | 7/2008 |
| WO | 2011110531 | 9/2011 |

OTHER PUBLICATIONS

Abdel-Magid et al., J. Org. Chem., 1996; 61: 3849-3862.*
Swanson, Rev. Clin. Basic. Pharm, 1985; 5(1-2): 1-33 (abstract only).*
Dilusha, et al., Reductive amination of carbohydrates using NaBH(OAc)3, Anal Bioanal Chem 381(6):1130-1137 (2005).
Abdel-Magid AF and SJ Mehrman., A Review on the Use of Sodium Triacetoxyborohydride in the Reductive Amination of Ketones and Aldehydes, Organic Process Res & Dev 10(5):971-1031 (2006).
Kristiansen CarbohydratePolymers 86 1595 2011 (Kristiansen et al., 2011;86:1595-1601).
Kristiansen CarbohydrateRes 345 1264 2010 (Kristiansen et al., 2010;345:1264-1271).

* cited by examiner

*Primary Examiner* — Gary B Nickol
*Assistant Examiner* — Lakia J Jackson-Tongue
(74) *Attorney, Agent, or Firm* — Barbara J. Carter

(57) ABSTRACT

The present invention relates to a process for conjugation of an antigen.

12 Claims, 4 Drawing Sheets

Figure 2
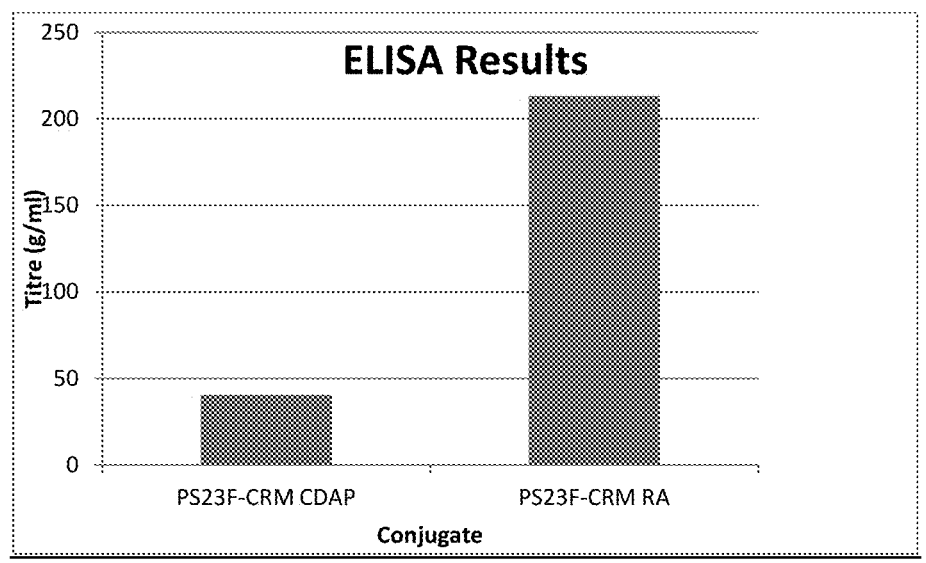
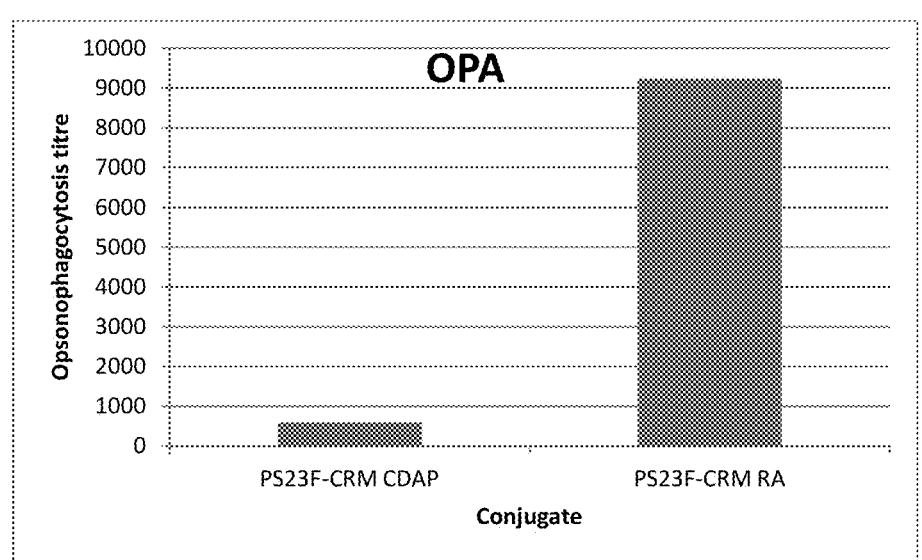

CONJUGATION PROCESS

This application is filed pursuant to 35 U.S.C. § 371 as a U.S. National Phase Application of International Patent Application Ser. No. PCT/EP2012/053715 filed Mar. 5, 2012, which claims priority to United Kingdom Application No. GB1103836.1 filed Mar. 7, 2011; the contents of each of the foregoing applications are hereby incorporated by reference.

BACKGROUND

Children less than 2 years of age do not mount an immune response to most polysaccharide vaccines, so it has been necessary to render the polysaccharides immunogenic by chemical conjugation to a protein carrier. Coupling the polysaccharide, a T-independent antigen, to a protein, a T-dependent antigen, confers upon the polysaccharide the properties of T dependency including isotype switching, affinity maturation, and memory induction.

*Streptococcus pneumoniae* is a Gram-positive bacterium responsible for considerable morbidity and mortality (particularly in the young and aged), causing invasive diseases such as pneumonia, bacteraemia and meningitis, and diseases associated with colonisation, such as acute Otitis media. The rate of pneumococcal pneumonia in the US for persons over 60 years of age is estimated to be 3 to 8 per 100,000. In 20% of cases this leads to bacteraemia, and other manifestations such as meningitis, with a mortality rate close to 30% even with antibiotic treatment.

Pneumococcus is encapsulated with a chemically linked polysaccharide which confers serotype specificity. There are 90 known serotypes of pneumococci, and the capsule is the principle virulence determinant for pneumococci, as the capsule not only protects the inner surface of the bacteria from complement, but is itself poorly immunogenic. Polysaccharides are T-independent antigens, and cannot be processed or presented on MHC molecules to interact with T-cells. They can however, stimulate the immune system through an alternate mechanism which involves cross-linking of surface receptors on B cells.

It was shown in several experiments that protection against invasive pneumococci disease is correlated most strongly with antibody specific for the capsule, and the protection is serotype specific.

*Streptococcus pneumoniae* is the most common cause of invasive bacterial disease and Otitis media in infants and young children. Likewise, the elderly mount poor responses to pneumococcal vaccines [Roghmann et al., (1987), J. Gerontol. 42:265-270], hence the increased incidence of bacterial pneumonia in this population [Verghese and Berk, (1983) Medicine (Baltimore) 62:271-285].

Conjugation of *Streptococcus pneumoniae* saccharides using cyanoborohydride ions is known, for example WO87/06838. However cyanoborohydride ions have several disadvantages including a relatively slow reaction time and the possible contamination of the product with cyanide (Ahmed F. et al J. Org. Chem., 1996, 61:3849-3862). The slow reaction time using this reagent was addressed in EP1035137 which describes an attempt to improve the reaction time of this conjugation process through use of microwave radiation.

Ahmed et al have described the reductive amination of aldehydes and ketones with sodium triacetoxyborohydride ($NaBH(OAc)_3$) (J. Org. Chem., 1996, 61:3849-3862). Similarly the reductive amination of carbohydrates using $NaBH(OAc)_3$ was described by Dalpathado et al (Anal. Bioanal. Chem (2005) 281:130-1137).

Accordingly the present invention provides an improved process for conjugation of an antigen by reductive amination using triacetoxyborohydride ($BH(OA)_3$) anions at the reducing agent. The inventors have discovered that this reducing agent is suitable for use to conjugate bacterial saccharides to carrier proteins; in particular this is quicker than the equivalent reaction using cyanoborohydride ions and does not produce toxic by-products.

SUMMARY OF THE INVENTION

In a first aspect of the invention there is provided a process for conjugation of an antigen comprising the steps of
a) activating the antigen to form an activated antigen;
b) reacting the activated antigen and a carrier protein to form an imine group linking the activated antigen to the carrier protein; and
c) reducing the imine group using a reducing agent comprising a triacetoxyborohydride moiety to form a conjugated antigen; or
a) activating the antigen to form an activated antigen;
b') reacting the activated antigen and a linker to form an imine group linking the activated antigen to the linker;
c') reducing the imine group using a reducing agent comprising a triacetoxyborohydride moiety to form an antigen-linker; and
d) reacting the antigen-linker with a carrier protein to form a conjugated antigen;
wherein the antigen originates from *Streptococcus pneumoniae, Haemophilus influenzae, Neisseria meningitidis, Staphylococcus aureus, Enterococcus faecium, Enterococcus faecalis, Salmonella* Vi, or *Staphylococcus epidermidis*.

In a second aspect of the invention there is provided a process for conjugation of an antigen comprising the steps of
a) activating the antigen to form an activated antigen;
a') lyophilising the activated antigen and a carrier protein followed by reconstitution in DMSO or DMF;
b) reacting the activated antigen and the carrier protein to form an imine group linking the activated antigen to the carrier protein; and
c) reducing the imine group using a reducing agent comprising a triacetoxyborohydride moiety to form a conjugated antigen;
or
a) activating the antigen to form an activated antigen;
a') lyophilising the activated antigen and a linker followed by reconstitution in DMSO or DMF;
b') reacting the activated antigen and the linker to form an imine group linking the activated antigen to the carrier protein; and
c') reducing the imine group using a reducing agent comprising a triacetoxyborohydride moiety to form an antigen-linker;
d) reacting the antigen-linker with a carrier protein to form a conjugated antigen.

In a third aspect of the invention there is provided an immunogenic composition comprising the conjugated antigen mixed with a pharmaceutically acceptable excipient.

In a fourth aspect of the invention there is provided an immunogenic composition obtainable by the process of the invention.

In a fifth aspect of the invention there is provided an immunogenic composition obtained by the process of the invention.

In an sixth aspect of the invention there is provided a vaccine comprising the immunogenic composition of the invention.

In a seventh aspect of the invention there is provided a use of the immunogenic composition of or the vaccine of the invention in the prevention or treatment of disease for example bacterial disease.

In an eighth aspect of the invention there is provided a use of the immunogenic composition or the vaccine of the invention in the prevention or treatment of a disease selected from the group consisting of bacterial meningitis, pneumococcal disease, *Haemophilus influenzae* disease, meningococcal disease, staphylococcal disease, enterococcal disease and *Salmonella*.

In an ninth aspect of the invention there is provided a use of the immunogenic composition of the invention or the vaccine of the invention in the preparation of a medicament for the prevention or treatment of disease for example bacterial disease.

In a tenth aspect of the invention there is provided a use of the immunogenic composition of the invention or the vaccine of the invention in the preparation of a medicament for the prevention or treatment of a disease selected from the group consisting of bacterial meningitis, pneumococcal disease, *Haemophilus influenzae* disease, meningococcal disease, staphylococcal disease, enterococcal disease and *Salmonella*.

In a eleventh aspect of the invention there is provided a method of preventing or treating infection for example bacterial infection comprising administering the immunogenic composition of the invention or the vaccine of the invention to a patient.

In a twelfth aspect of the invention there is provided a method of preventing or treating a disease selected from the group consisting of bacterial meningitis, pneumococcal disease, *Haemophilus influenzae* disease, meningococcal disease, staphylococcal disease, enterococcal disease and *Salmonella* comprising administering the immunogenic composition of the invention or the vaccine of the invention to a patient.

DESCRIPTION OF FIGURES

FIG. 2. Comparison of immunogenicity of 23F conjugates using either CDAP or reductive amination conjugation. Graph a) describes the results of an ELISA assay. Graph b) describes the results of an opsonophagocytosis assay.

DETAILED DESCRIPTION OF THE INVENTION

Figure 1:
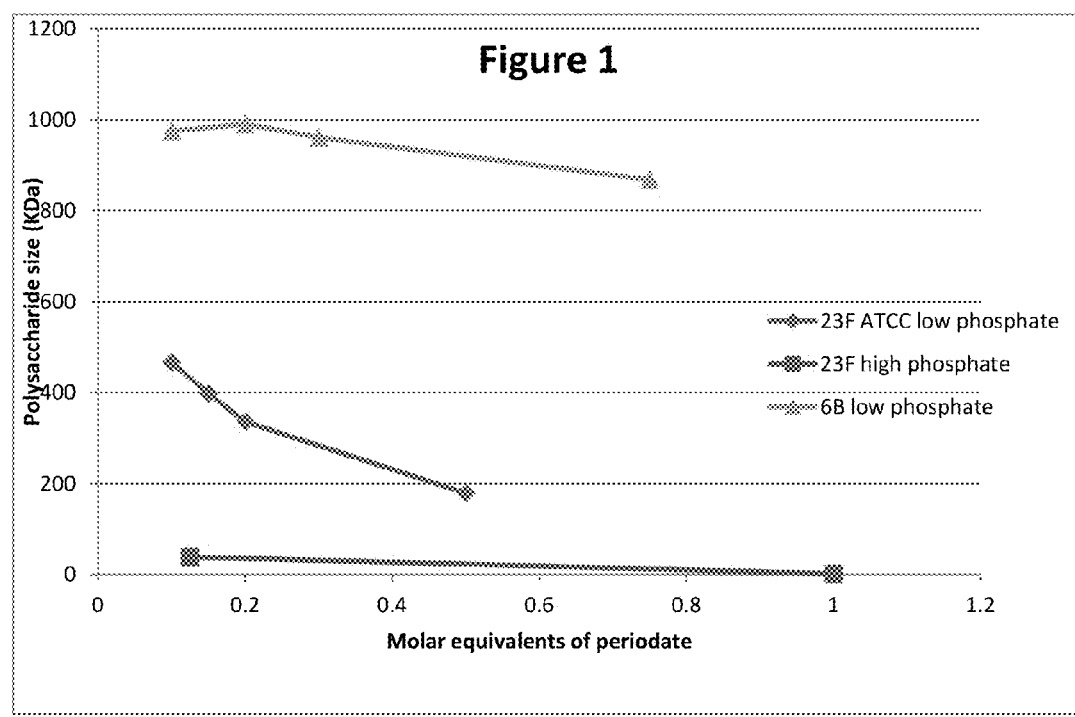
FIG. 1. Size of 23F and 6B polysaccharides following periodate treatment. The line marked with triangles shows the size of 6B in 10 mM phosphate buffer, the line marked with diamonds shows the size of 23F in 10 mM phosphate buffer and the line marked with squares shows the size of 23F in 100 mM phosphate buffer.

The invention relates to an improved process for conjugating an antigen to a carrier protein. In particular, the invention provides a process for conjugating an antigen comprising the steps of a) activating the antigen to form an activated antigen;
b) reacting the activated antigen and a carrier protein to form an imine group linking the activated antigen to the carrier protein; and
c) reducing the imine group using a reducing agent comprising a triacetoxyborohydride moiety to form a conjugated antigen;
or
a) activating the antigen to form an activated antigen;
b') reacting the activated antigen and a linker to form an imine group linking the activated antigen to the linker;
c') reducing the imine group using a reducing agent comprising a triacetoxyborohydride moiety to form an antigen-linker; and
d) reacting the antigen-linker with a carrier protein to form a conjugated antigen;
wherein the antigen originates from *Streptococcus pneumoniae, Haemophilus influenzae, Neisseria meningitidis, Staphylococcus aureus, Enterococcus faecium, Enterococcus faecalis, Salmonella* Vi, or *Staphylococcus epidermidis*.

In an embodiment the process of the invention comprises steps a), b) and c).

The invention further provides a process for conjugation of an antigen comprising the steps of
a) activating the antigen to form an activated antigen;
a') lyophilising the activated antigen and a carrier protein followed by reconstitution in DMSO or DMF;
b) reacting the activated antigen and the carrier protein to form an imine group linking the activated antigen to the carrier protein; and
c) reducing the imine group using a reducing agent comprising a triacetoxyborohydride moiety to form a conjugated antigen;
or
a) activating the antigen to form an activated antigen;
a') lyophilising the activated antigen and a linker followed by reconstitution in DMSO or DMF;
b') reacting the activated antigen and the linker to form an imine group linking the activated antigen to the carrier protein; and
c') reducing the imine group using a reducing agent comprising a triacetoxyborohydride moiety to form an antigen-linker;
d) reacting the antigen-linker with a carrier protein to form a conjugated antigen.

In a further embodiment the process of the invention comprises steps a), a'), b) and c).

For the purposes of the invention the term 'activating the antigen' refers to any process which introduces carbonyl groups onto the antigen, this process may include oxidation, for example oxidation with periodate, acid hydrolysis or chemical treatment. For the purposes of the invention the term 'activated antigen' refers to an antigen which has been altered by the process of 'activating the antigen'.

Step b) or b') may occur via the following reaction scheme:
R—CHO+H$_2$N—R'→R—CH═NH—R' wherein R—CHO is the antigen and H$_2$N—R' is the carrier protein.

Step c) or c') may occur via the following reaction scheme:
R—CH═NH—R'→R—CH$_2$—NH—R'.

A reducing agent is an agent which is capable of reducing an imine group, preferably the reducing agent reduces imine groups in preference to aldehyde groups. Reducing agents of the invention comprise a triacetoxyborohydride moiety (BH(OAc)$_3$), for example reducing agents of the invention may comprise sodium triacetoxyborohydride (NaBH(OAc)$_3$) or potassium triacetoxyborohydride (KBH(OAc)$_3$). Preferably the reducing agent does not contain a cyanoborohydride moeity, preferably the reducing agent does not comprise sodium cyanoborohydride.

For the purposes of the invention the term 'conjugated antigen' indicates an antigen linked covalently to a carrier protein.

Lyophilisation of the activated antigen and the carrier protein may refer to co-lyophilisation i.e. mixing the activated antigen and the carrier protein together and lyophilising them in the same container, or this may refer to lyophilising the activated antigen and the carrier protein separately and combining them together after lyophilisation.

In one embodiment the antigen is a bacterial saccharide. In a further embodiment the antigen is a bacterial capsular saccharide.

The term "saccharide" throughout this specification may indicate polysaccharide, oligosaccharide or teichoic acid and includes all three. It may indicate lipopolysaccharide (LPS) or lipooliogosaccharide (LOS). Before use Polysaccharides may be isolated from a source strain or isolated from the source strain and sized to some degree by known methods (see for example EP497524 and EP497525; Shousun Chen Szu et al.—Carbohydrate Research Vol 152 p 7-20 (1986)) for instance by microfluidisation. Oligosaccharides have a low number of repeat units (typically 5-30 repeat units).

In an embodiment the bacterial saccharide originates from *S. pneumoniae, H. influenzae, N, meningitidis, S. aureus, E. faecalis, E. faecium, Salmonella* Vi or *S. epidermidis*. In a further embodiment the bacterial saccharide originates from *S. pneumoniae, H. Influenzae* or *N. meningitidis*. In a further embodiment the bacterial saccharide originates from *S. pneumoniae*. In a further embodiment the bacterial saccharide originates from *H. influenzae*. In a yet further embodiment the bacterial saccharide is a bacterial capsular saccharide selected from a list consisting of: *N. meningitidis* serogroup A (MenA), B (MenB), C (MenC), W135 (MenW) or Y (MenY), Group B *Streptococcus* group Ia, Ib, II, III, IV, V, VI, or VII, *Staphylococcus aureus* type 5, *Staphylococcus aureus* type 8, *Salmonella typhi* (Vi saccharide), *Vibrio cholerae, H. influenzae* type b and from *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F or 33F.

In a further embodiment the bacterial capsular saccharide is from an *S. pneumoniae* serotype selected from the group consisting of 5, 6B, 6A, 7F, 9V, 14, 19F and 23F. In one embodiment the bacterial capsular saccharide is *S. pneumoniae* capsular saccharide 23F. In one embodiment the bacterial capsular saccharide is *S. pneumoniae* capsular saccharide 6B. In one embodiment the bacterial capsular saccharide is *S. pneumoniae* capsular saccharide 6A.

In a further embodiment the bacterial saccharide is *Haemophilus influenzae* b (Hib) polysaccharide or oligosaccharide.

In one embodiment the antigen is a protein or a fragment of a protein. In one embodiment the protein or fragment of a protein originates from *S. pneumoniae, H. influenzae, N, meningitidis, S. aureus, E. faecalis, E. faecium, Salmonella* Vi or *S. epidermidis*. In a further embodiment the protein or fragment of a protein originates from *S. pneumoniae, H. Influenzae* or *N. meningitidis*.

The term "carrier protein" is intended to cover both small peptides and large polypeptides (>10 kDa). The carrier protein may be any peptide or protein. It may comprise one or more T-helper epitopes. The carrier protein may be tetanus toxoid (TT), tetanus toxoid fragment C, non-toxic mutants of tetanus toxin [note all such variants of TT are considered to be the same type of carrier protein for the purposes of this invention], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from *N. meningitidis* serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761), *H. influenzae* Protein D (EP594610 and WO 00/56360), pneumococcal PhtA (WO 98/18930, also referred to Sp36), pneumococcal PhtD (disclosed in WO 00/37105, and is also referred to Sp036D), pneumococcal PhtB (disclosed in WO 00/37105, and is also referred to Sp036B), or PhtE (disclosed in WO00/30299 and is referred to as BVH-3).

In one embodiment of the invention the carrier protein is selected from the group consisting of: tetanus toxoid (TT), fragment C of tetanus toxoid, diphtheria toxoid (DT), CRM197, Pneumolysin (Ply), protein D, PhtD, PhtDE and N19. In a further embodiment the carrier protein is CRM197. In a still further embodiment the carrier protein is tetanus toxoid.

In an embodiment the antigen is conjugated directly to the carrier protein. In a further embodiment the antigen is conjugated to the carrier protein via the addition of a hetero- or homo-bifunctional linker using the chemistry of the invention. One end of the linker will react with the activated antigen by reductive amination, however the other end of the linker may react with the carrier protein using any type of chemistry. For this reason the linker will contain at least one reactive amino group, if the linker is homo-bifunctional it will contain two reactive amino groups, if the linker is hetero-bifunctional it will contain one reactive amino group and a different reactive group, in one embodiment this second reactive group is a reactive carbonyl group. In one embodiment the linker is between 1 and 20 Angstroms in length. In a further embodiment the linker has between 4 and 20, 4 and 12, or 5 and 10 carbon atoms. A possible linker is adipic acid dihydrazide (ADH). Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. No. 4,673,574, U.S. Pat. No. 4,808,700), hexane diamine and 6-aminocaproic acid (U.S. Pat. No. 4,459,286).

In general the following types of chemical groups on the carrier protein can be used for coupling/conjugation as the second reactive group:
A) Carboxyl (for instance via aspartic acid or glutamic acid). In one embodiment this group is linked to an amino group on a linker with carbodiimide chemistry e.g. with EDAC (1-Ethyl-3-(3-dimethylaminopropyl)carbodiimide)).
   Note: instead of EDAC above, any suitable carbodiimide may be used.
B) Amino group (for instance via lysine). In one embodiment this group is linked to a carboxyl group on an a linker with carbodiimide chemistry e.g. with EDAC. In another embodiment this group is linked to linkers having hydroxyl groups activated with CDAP or CNBr; or a carbonyl group; or a succinimide ester group.
C) Sulphydryl (for instance via cysteine). In one embodiment this group is linked to a bromo or chloro acetylated linker or to a linker having maleimide groups.
D) The protein could be modified to contain an alkynyl or azide group this could be conjugated to the linker using the 'click' chemistry (described in Tetrahedron letters (June 2005) 46:4479-4482).

In one embodiment steps b) and c) or b') and c') occur simultaneously.

In a further embodiment step c) and/or step c') and/or step b) and/or step b') is carried out in the presence of a non aqueous solvent. In a further embodiment step c) and/or step c') and/or step b) and/or step b') is carried out in solvent which us essentially water free. For example the reaction may take place in the presence of dimethylsulphoxide (DMSO) or dimethylformamide (DMF). In one embodiment step c) and/or step c') and/or step b) and/or step b') takes place in a solution consisting essentially of DMSO or DMF. If the carrier protein and the activated antigen have been lyophilised, DMSO or DMF may be used to reconstitute the carrier protein and activated antigen.

In an embodiment step c), and/or step c') takes place in less than 30 hours, less than 25 hours, less than 20 hours, less than 19 hours, less than 18 hours or less than 17 hours.

In an embodiment step c), and/or step and c') takes place in between 15 mins and 30 hours, between 10 hours and 25 hours, between 8 hours and 20 hours, between 10 hours and 20 hours or between 14 hours and 19 hours. In a further embodiment step c) and/or step c') take place in around 16 hours.

In an embodiment step c) and/or c') does not result in the production of cyanide ions. For example reductive amination using a reducing agent comprising a cyanoborohydride moiety may result in the production of cyanide ions; these can be toxic if used in vaccination.

In an embodiment the antigen and the carrier protein are mixed together before step b). This can occur during step a'), in general however the carrier protein and the antigen will be mixed together after step a).

In one embodiment the antigen and the carrier protein are lyophilised before step b), preferably this occurs after step a). In one embodiment the activated antigen is lyophilised after step a), the carrier protein is also lyophilised and the activated antigen and the carrier protein are reconstituted in the same solution, this acts as mixing the antigen and the carrier protein together.

In one embodiment the lyophilisation takes place in the presence of a non-reducing sugar, possible non-reducing sugars include sucrose, lactose, trehalose, raffinose, stachyose, melezitose, dextran, mannitol, lactitol and palatinit. In an embodiment the sugar is selected from the group consisting of sucrose, trehalose, and mannitol.

In one embodiment between 0.2 and 5, between 0.5 and 3 or between 0.9 and 2.6, between 0.5 and 0.8, between 0.2 and 1.0, between 2 and 3 or between 1 and 4 molar equivalent of reducing agent is used in step c) or c'). For the purposes of the invention using 1 molar equivalent of reducing agent corresponds to using one mole of reducing agent per one mole of saccharide repeating units. In a further embodiment around 2.5 molar equivalent or between 1 and 3 molar equivalent of reducing agent is used in step c) or step c').

In one embodiment the ratio of carrier protein:antigen before step c) and/or c') is between 0.4:1 and 2:1. In an embodiment the ratio of carrier protein:antigen before step c) or c') is between 1:1 and 2:1. In a further embodiment the ratio of carrier protein:antigen before step c) and/or c') for PS23F or PS6B is between 1:1 and 2:1, between 0.4/1 and 2.5/1, between 2.0/1 and 2.5/1, or between 0.2/1 and 1.5/1. In an embodiment the ratio of carrier protein:antigen after step c) and/or c') is between 0.8:1 and 3.5:1. In a further embodiment the ratio of carrier protein:antigen after step c) and/or c') is between 1.3:1 and 2.7:1. In a further embodiment the ratio of carrier protein:antigen after step c) and/or c') is between 1:1 and 1.5:1.

At the end of step c) or c') there may be unreacted carbonyl groups remaining in the conjugated antigens, these may be capped using a suitable capping agent. In one embodiment this capping agent is sodium borohydride ($NaBH_4$), for example the product of step c) or c') may be reacted with sodium borohydride for 15 mins-15 hrs, 15 mins-45 mins, 2-10 hrs or 3.5 hrs, around 30 mins or around 4 hrs. In a further embodiment capping is achieved by mixing the product of step c) with 1 to 10 molar equivalents, between 1 to 5, between 1.5 and 2.5, or around 2 molar equivalents of $NaBH_4$.

In one embodiment step a) comprises reacting the antigen with periodate. The term 'periodate' includes both periodate and periodic acid. This term also includes both metaperiodate ($IO_4^-$) and orthoperiodate ($IO_6^{5-}$), however in one particular embodiment the periodate used in the method of the invention is metaperiodate. The term 'periodate' also includes the various salts of periodate including sodium periodate and potassium periodate. In one embodiment the periodate used is sodium metaperiodate. When an antigen reacts with periodate, periodate oxidises vicinal hydroxyl groups to form carbonyl or aldehyde groups and causes cleavage of a C—C bond. For this reason the term 'reacting an antigen with periodate' includes oxidation of vicinal hydroxyl groups by periodate.

In one embodiment step a) comprises reacting the antigen with 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate, in a further embodiment step a) comprises reacting the antigen with 0.0001-0.8 molar equivalents of periodate.

In one embodiment the buffer used in step a) is a buffer which does not contain an amine group. In one embodiment the buffer is selected from the list consisting of phosphate buffer, borate buffer, acetate buffer, carbonate buffer, maleate buffer and citrate buffer. In a second embodiment the buffer is an inorganic buffer. The term inorganic buffer includes any buffer solution wherein the buffering capacity is due to the presence of a compound which does not contain carbon. Inorganic buffers of the invention include phosphate buffer and borate buffer. In one embodiment the buffer is phosphate buffer.

In one embodiment the buffer has a concentration between 1-100 mM, 5-80 mM, 1-50 mM, 1-25 mM, 10-40 mM, 1-10 mM, 5-15 mM, 8-12 mM, 10-20 mM, 5-20 mM, 10-50 mM, around 10 mM or around 20 mM. In a further embodiment the pH in step a) is pH 3.0-8.0, pH 5.0-7.0, pH 5.5-6.5, pH 5.8-6.3, or around pH 6.0.

In one embodiment step a) is carried out in the dark, for example the container containing the reaction mixture may be covered with a material capable of reflecting light for example aluminium foil.

The antigen may be a native bacterial saccharide or may be a bacterial saccharide that has been reduced in size by a factor of no more than ×2, ×4, ×6, ×8, ×10 or ×20 (for instance by microfluidization [e.g. by Emulsiflex C-50 apparatus] or other known technique [for instance heat, chemical, oxidation, sonication methods]). In one embodiment the antigen is a bacterial saccharide which is microfluidised before step a). Oligosaccharides may have been reduced in size substantially further [for instance by known heat, chemical, or oxidation methods].

For the purposes of the invention, "native bacterial saccharide" refers to a bacterial saccharide that has not been subjected to a process, the purpose of which is to reduce the size of the saccharide. A bacterial saccharide can become slightly reduced in size during normal purification procedures. Such a saccharide is still native. Only if the bacterial saccharide has been subjected to techniques which reduce a saccharide in size would the polysaccharide not be considered native.

The weight-average molecular weight of a bacterial saccharide suitable for conjugation by the process of the invention may be between 20 kDa and 2000 kDa, between 30 kDa and 1000 kDa, between 40 kDa and 500 kDa, between 50 kDa and 400 kDa, between 75 kDa and 300 kDa or between 1000 kDa and 2000 kDa. In the case of the native 23F capsular saccharide from S. pneumoniae, the average molecular weight of the native polysaccharide is between 750-1500 kDa or 1200-1300 kDa. In the case of the native Hib saccharide, the average molecular weight of the native polysaccharide is between 100 and 250 kDa. The molecular weight or average molecular weight of a saccharide herein refers to the weight-average molecular weight (Mw) of the bacterial saccharide measured prior to conjugation and is measured by MALLS. The MALLS technique is well known in the art. MALLS analyses may be carried out using a TSKGMPwxI and 50 mM Na/K PO4, 200 mM NaCl pH 7.0 as elution buffer with 0.75 ml/min using RI/DAWN-EOS detector. In an embodiment, the polydispersity of a bacterial saccharide is 1-1.5, 1-1.3, 1-1.2, 1-1.1 or 1-1.05 and after conjugation to a carrier protein, the polydispersity of the conjugated bacterial saccharide is 1.0-2.5, 1.0-2.0. 1.0-1.5, 1.0-1.2, 1.5-2.5, 1.7-2.2 or 1.5-2.0. All polydispersity measurements are generated by MALLS.

Treatment with periodate may lead to a reduction in the size of the bacterial saccharide (sizing effect). In one embodiment the process of the invention reduces this sizing effect. This is seen for the 23F bacterial saccharide from *Streptococcus pneumoniae* (as in example 1). For this reason, in one embodiment the average molecular weight of a bacterial saccharide of the invention is between 1-1100 kDa, 100-470 kDa, 200-300 kDa, 600-1100 kDa or 800-1000 kDa after step a) (measured by MALLS as described above). In one embodiment the average molecular weight of the 23F saccharide is between 100-470 kDa or 200-300 kDa after step a). In one embodiment the average molecular weight of the Hib bacterial saccharide is between 1 and 50 kDa or between 5 and 10 kDa after step a).

The invention also provides a further step e) of purifying the conjugated antigen, step e) may comprise diafiltration, for example diafiltration with a cut-off of 100 kDa. In addition or alternatively step e) may comprise ion exchange chromatography. In a further embodiment step e) may comprise size exclusion chromatography. In a further embodiment step e) may comprise purifying the conjugated antigen using gel permeation. In one embodiment the process comprises a further step f), wherein the conjugate is sterile filtered.

The conjugated antigen may also be mixed with further antigens. In one embodiment the further antigens comprise at least 7, 8, 9, 10, 11, 12, 13, 14, 15, 16, 17, 18, 19 or 20 *S. pneumoniae* saccharides selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In one embodiment the further antigens comprise *S. pneumoniae* saccharides 4, 6B, 9V, 14, 18C, 19F and 23F. In one embodiment the further antigens comprise *S. pneumoniae* saccharides 4, 6B, 9V, 14, 18C and 19F. In one embodiment the further antigens comprise *S. pneumoniae* saccharides 4, 9V, 14, 18C, 19F and 23F. In one embodiment the further antigens comprise *S. pneumoniae* saccharides 1, 4, 5, 6B, 7F, 9V, 14, 18C, 19F and 23F. In one embodiment the further antigens comprise *S. pneumoniae* saccharides 1, 4, 5, 6B, 7F, 9V, 14, 18C, and 19F. In one embodiment the further antigens comprise *S. pneumoniae* saccharides 1, 4, 5, 7F, 9V, 14, 18C, 19F and 23F. In one embodiment the further antigens comprise *S. pneumoniae* saccharides 1, 3, 4, 5, 6A, 6B, 7F, 9V, 14, 18C, 19A, 19F and 23F. In one embodiment the further antigens comprise *S. pneumoniae* saccharides 1, 3, 4, 5, 6A, 6B, 7F, 9V, 14, 18C, 19A and 19F. In one embodiment the further antigens comprise *S. pneumoniae* saccharides 1, 3, 4, 5, 6A, 7F, 9V, 14, 18C, 19A, 19F and 23F. In one embodiment the further antigens comprise *S. pneumoniae* saccharides 1, 4, 5, 6A, 6B, 7F, 9V, 14, 18C, 19A, 19F and 23F. In one embodiment the further antigens comprise *S. pneumoniae* saccharides 1, 4, 5, 6A, 6B, 7F, 9V, 14, 18C, 19A and 19F. In one embodiment the further antigens comprise *S. pneumoniae* saccharides 1, 4, 5, 6A, 7F, 9V, 14, 18C, 19A, 19F and 23F.

Any of the saccharides listed as 'further antigens' are optionally conjugated to a carrier protein either by the process of the invention or by a different process. Optionally these further antigens are conjugated to the carrier proteins listed above.

In an embodiment, the further antigens comprise *S. pneumoniae* capsular saccharide 1 conjugated to protein D or CRM197. In an embodiment, the further antigens comprise *S. pneumoniae* capsular saccharide 3 conjugated to protein D, CRM197, pneumolysin or PhtD or fragment or fusion protein thereof. In an embodiment, the further antigens comprise *S. pneumoniae* capsular saccharide 4 conjugated to protein D or CRM197. In an embodiment, the further antigens comprise *S. pneumoniae* capsular saccharide 5 conjugated to protein D or CRM197. In an embodiment, the further antigens comprise *S. pneumoniae* capsular saccharide 6B conjugated to protein D or CRM197. In an embodiment, the further antigens comprise *S. pneumoniae* capsular saccharide 7F conjugated to protein D or CRM197. In an embodiment, the further antigens comprise *S. pneumoniae* capsular saccharide 9V conjugated to protein D or CRM197. In an embodiment, the further antigens comprise *S. pneumoniae* capsular saccharide 14 conjugated to protein D or CRM197. In an embodiment, the further antigens comprise *S. pneumoniae* capsular saccharide 23F conjugated to protein D or CRM197. In an embodiment, the further antigens comprise *S. pneumoniae* capsular saccharide 18C conjugated to tetanus toxoid or CRM197. In an embodiment, the further antigens comprise S. pneumoniae capsular saccharide 19A conjugated to pneumolysin or CRM197. In an embodiment, the further antigens comprise S. pneumoniae capsular saccharide 22F conjugated to CRM197 or PhtD or fragment of fusion protein thereof. In an embodiment, the further antigens comprise S. pneumoniae capsular saccharide 6A conjugated to pneumolysin or a H. influenzae protein, optionally protein D or PhtD or fusion protein thereof or CRM197. In an embodiment, the further antigens comprise S. pneumoniae capsular saccharide 6C conjugated to pneumolysin or a H. influenzae protein, optionally protein D or PhtD or fusion protein thereof or CRM197. In an embodiment, the further antigens comprise S. pneumoniae capsular saccharide 19F conjugated to Diphtheria toxoid (DT).

The further antigens may also comprise Streptococcus pneumoniae proteins. In one embodiment the further antigens comprise at least 1 protein selected from the group consisting of the Poly Histidine Triad family (PhtX), Choline Binding protein family (CbpX), CbpX truncates, LytX family, LytX truncates, CbpX truncate-LytX truncate chimeric proteins (or fusions), pneumolysin (Ply), PspA, PsaA, Sp128, Sp101, Sp130, Sp125 and Sp133. In one embodiment the further antigens comprise PhtD and/or Ply.

The further antigens may also comprise antigens from further bacterial species. In one embodiment the vaccine or immunogenic composition comprises antigens originating from S. pneumoniae, H. influenzae, N. meningitidis, E. coli, M. cattarhalis, tetanus, diphtheria, pertussis, S. epidermidis, enterococci, Pseudomonas or S. aureus.

In one embodiment the further antigens comprise M. cattarhalis antigens, preferred M. cattarhalis antigens are: OMP106 [WO 97/41731 (Antex) & WO 96/34960 (PMC)]; OMP21; LbpA & LbpB [WO 98/55606 (PMC)]; TbpA & TbpB [WO 97/13785 & WO 97/32980 (PMC)]; CopB [Helminen M E, et al. (1993) Infect. Immun. 61:2003-2010]; UspA1/2 [WO 93/03761 (University of Texas)]; and OmpCD. Examples of non-typeable Haemophilus influenzae antigens which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and TbpB; Hia; Hmw1,2; Hap; and D15.

In a further embodiment the further antigens comprise Diphtheria toxoid (DT), tetanus toxoid (TT), and pertussis components [typically detoxified Pertussis toxoid (PT) and filamentous haemagglutinin (FHA) with optional pertactin (PRN) and/or agglutinin 1+2 and/or agglutinogen 1+2], for example the marketed vaccine INFANRIX-DTPa™ (SmithKlineBeecham Biologicals) which contains DT, TT, PT, FHA and PRN antigens, or with a whole cell pertussis component for example as marketed by SmithKlineBeecham Biologicals s.a., as Tritanrix™. In a further embodiment the further antigens comprise Hepatitis B surface antigen (HepB).

In a further embodiment the further antigens comprise the PRP capsular saccharide of H. influenzae (Hib).

In a further embodiment the further antigens comprise at least one capsular saccharide from N. meningitidis A, C, W or Y. In a further embodiment the further antigens comprise at least one conjugate of a capsular saccharide from N. meningitidis A, C, W, Y or B.

The conjugated antigen may also be mixed with an adjuvant. Suitable adjuvants include, but are not limited to, aluminium salts (aluminium phosphate or aluminium hydroxide), monophosphoryl lipid A (for example 3D-MPL), saponins (for example QS21), oil in water emulsions, blebs or outer membrane vesicle preparations from Gram negative bacterial strains (such as those taught by WO02/09746), lipid A or derivatives thereof, alkyl glucosamide phosphates or combinations of two or more of these adjuvants.

In a further embodiment the conjugated antigen of the invention is mixed with a pharmaceutically acceptable excipient to form an immunogenic composition.

The invention further provides an immunogenic composition obtainable by the process of the invention. The invention also provides an immunogenic composition obtained by the process of the invention. In one embodiment the pharmaceutical acceptable excipient does not contain sodium chloride. In one embodiment the pharmaceutical excipient comprises a buffer selected from the group consisting of phosphate, maleate, tris, or citrate. In a further embodiment the buffer is maleate buffer.

The immunogenic composition of the invention may comprise further antigens, in particular those described as 'further antigens' above. The immunogenic composition of the invention may comprise an adjuvant. In one embodiment the adjuvant is an aluminium salt.

The invention also provides a vaccine comprising the immunogenic composition of the invention.

The vaccine preparations containing immunogenic compositions of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is possible (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). In addition to a single route of administration, 2 different routes of administration may be used. For example, saccharides or saccharide conjugates may be administered IM (or ID) and bacterial proteins may be administered IN (or ID). In addition, the vaccines of the invention may be administered IM for priming doses and IN for booster doses.

The content of protein antigens in the vaccine will typically be in the range 1-100 µg, optionally 5-50 µg, most typically in the range 5-25 µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms an optional feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. No. 5,480,381, U.S. Pat. No. 5,599,302, U.S. Pat. No. 5,334,144, U.S. Pat. No. 5,993,412, U.S. Pat. No. 5,649,912, U.S. Pat. No. 5,569,189, U.S. Pat. No. 5,704,911, U.S. Pat. No. 5,383,851, U.S. Pat. No. 5,893,397, U.S. Pat. No. 5,466,220, U.S. Pat. No. 5,339,163, U.S. Pat. No. 5,312,335, U.S. Pat. No. 5,503,627, U.S. Pat. No. 5,064,413, U.S. Pat. No. 5,520,639, U.S. Pat. No. 4,596,556, U.S. Pat. No. 4,790,824, U.S. Pat. No. 4,941,880, U.S. Pat. No. 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are optionally present in as little as 0.1 to 10 µg or 0.1 to 5 µg per dose; and the saccharide (optionally conjugated) antigens may be present in the range of 0.01-1 µg, or between 0.01 to 0.5 µg of saccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

A further aspect of the invention is a method of preventing or treating infection for example bacterial infection comprising administering to the host an immunoprotective dose of the immunogenic composition or vaccine or kit of the invention. A further aspect of the invention is a method of preventing or treating a disease selected from the group consisting of bacterial meningitis, pneumococcal disease, *Haemophilus influenzae* disease, meningococcal disease, staphylococcal disease, enterococcal disease and *Salmonella* comprising administering to the host an immunoprotective dose of the immunogenic composition or vaccine or kit of the invention.

A further aspect of the invention is an immunogenic composition of the invention for use in the treatment or prevention of disease for example bacterial disease. A further aspect of the invention is an immunogenic composition of the invention for use in the treatment or prevention of a disease selected from the group consisting of bacterial meningitis, pneumococcal disease, *Haemophilus influenzae* disease, meningococcal disease, staphylococcal disease, enterococcal disease and *Salmonella*.

A further aspect of the invention is use of the immunogenic composition or vaccine or kit of the invention in the manufacture of a medicament for the treatment or prevention of disease for example bacterial disease. A further aspect of the invention is use of the immunogenic composition or vaccine or kit of the invention in the manufacture of a medicament for the prevention or treatment of a disease selected from the group consisting of bacterial meningitis, pneumococcal disease, *Haemophilus influenzae* disease, meningococcal disease, staphylococcal disease, enterococcal disease and *Salmonella*.

Around" or "approximately" are defined as within 10% more or less of the given figure for the purposes of the invention.

The terms "comprising", "comprise" and "comprises" herein are intended by the inventors to be optionally substitutable with the terms "consisting of", "consist of" and "consists of", respectively, in every instance.

Embodiments herein relating to "vaccine compositions" of the invention are also applicable to embodiments relating to "immunogenic compositions" of the invention, and vice versa. All references or patent applications cited within this patent specification are incorporated by reference herein.

In order that this invention may be better understood, the following examples are set forth. These examples are for purposes of illustration only, and are not to be construed as limiting the scope of the invention in any manner.

Embodiments of the invention are further described in the subsequent numbered paragraphs.

Paragraph 1. A process for conjugation of an antigen comprising the steps of
  a) activating the antigen to form an activated antigen;
  b) reacting the activated antigen and a carrier protein to form an imine group linking the activated antigen to the carrier protein; and
  c) reducing the imine group using a reducing agent comprising a triacetoxyborohydride moiety to form a conjugated antigen;

or
a) activating the antigen to form an activated antigen;
b') reacting the activated antigen and a linker to form an imine group linking the activated antigen to the linker;
c') reducing the imine group using a reducing agent comprising a triacetoxyborohydride moiety to form an antigen-linker; and
d) reacting the antigen-linker with a carrier protein to form a conjugated antigen;
wherein the antigen originates from *Streptococcus pneumoniae*, *Haemophilus influenzae*, *Neisseria meningitidis*, *Staphylococcus aureus*, *Enterococcus faecium*, *Enterococcus faecalis*, *Salmonella* Vi, or *Staphylococcus epidermidis*.

Paragraph 2. The process of paragraph 1 comprising the steps of
a) activating the antigen to form an activated antigen;
b) reacting the activated antigen and a carrier protein to form an imine group linking the activated antigen to the carrier protein; and
c) reducing the imine group using a reducing agent comprising a triacetoxyborohydride moiety to form a conjugated antigen;
wherein the antigen originates from *Streptococcus pneumoniae*, *Haemophilus influenzae*, *Neisseria meningitidis*, *Staphylococcus aureus*, *Enterococcus faecium*, *Enterococcus faecalis*, *Salmonella* Vi, or *Staphylococcus epidermidis*.

Paragraph 3. A process for conjugation of an antigen comprising the steps of
a) activating the antigen to form an activated antigen;
a') lyophilising the activated antigen and a carrier protein followed by reconstitution in DMSO or DMF;
b) reacting the activated antigen and the carrier protein to form an imine group linking the activated antigen to the carrier protein; and
c) reducing the imine group using a reducing agent comprising a triacetoxyborohydride moiety to form a conjugated antigen; or
a) activating the antigen to form an activated antigen;
a') lyophilising the activated antigen and a linker followed by reconstitution in DMSO or DMF;
b') reacting the activated antigen and the linker to form an imine group linking the activated antigen to the carrier protein; and
c') reducing the imine group using a reducing agent comprising a triacetoxyborohydride moiety to form an antigen-linker;
d) reacting the antigen-linker with a carrier protein to form a conjugated antigen.

Paragraph 4. The process of paragraph 3 comprising the steps of:
a) activating the antigen to form an activated antigen;
a') lyophilising the activated antigen and a carrier protein followed by reconstitution in DMSO or DMF;
b) reacting the activated antigen and the carrier protein to form an imine group linking the activated antigen to the carrier protein; and
c) reducing the imine group using a reducing agent comprising a triacetoxyborohydride moiety to form a conjugated antigen.

Paragraph 5. The process of any preceding paragraph wherein the reducing agent does not contain a cyanoborohydride moeity.

Paragraph 6. The process of any preceding paragraph wherein the antigen is a bacterial saccharide.

Paragraph 7. The process of any preceding paragraph wherein the antigen is a bacterial capsular saccharide.

Paragraph 8. The process of any one of paragraphs 1-7 wherein the antigen is a bacterial saccharide originating from *S. pneumoniae*, *H. influenzae*, *N. meningitidis*, *S. aureus*, *E. faecalis*, *E. faecium*, *Salmonella* Vi, or *S. epidermidis*.

Paragraph 9. The process of any one of paragraphs 7 or 8 wherein the antigen is a bacterial capsular saccharide from an *S. pneumoniae* serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F.

Paragraph 10. The process of any one of paragraphs 7-9 wherein the bacterial capsular saccharide is from an *S. pneumoniae* serotype selected from the group consisting of 5, 6B, 6A, 7F, 9V, 14, 19F and 23F.

Paragraph 11. The process of any one of paragraphs 7-10 wherein the bacterial capsular saccharide is *S. pneumoniae* capsular saccharide 23F.

Paragraph 12. The process of any one of paragraphs 7-11 wherein the bacterial capsular saccharide is *S. pneumoniae* capsular saccharide 6B.

Paragraph 13. The process of any one of paragraphs 7-12 wherein the bacterial capsular saccharide is *S. pneumoniae* capsular saccharide 6A.

Paragraph 14. The process of any one of paragraphs 7-8 wherein the bacterial saccharide is *Haemophilus influenzae* b (Hib) polysaccharide or oligosaccharide.

Paragraph 15. The process of any one of paragraphs 1-5 wherein the antigen is a protein or a fragment of a protein.

Paragraph 16. The process of any preceding paragraph wherein the carrier protein is a protein selected from the group consisting of tetanus toxoid (TT), fragment C of TT, diphtheria toxoid, CRM197, Pneumolysin, protein D, PhtD, PhtDE and N19.

Paragraph 17. The process of paragraph 16 wherein the carrier protein is CRM197.

Paragraph 18. The process of paragraph 16 wherein the carrier protein is tetanus toxoid.

Paragraph 19. The process of any preceding paragraph wherein the antigen is conjugated directly to the carrier protein.

Paragraph 20. The process of any one of paragraphs 1-18 wherein the antigen is conjugated to the carrier protein via a linker.

Paragraph 21. The process of paragraph 20 wherein the linker is between 1 and 20 Angstroms in length.

Paragraph 22. The process of any one of paragraphs 20-21 wherein the linker comprises an ADH linker.

Paragraph 23. The process of any preceding paragraph wherein steps b) and c), or steps b') and c') occur simultaneously.

Paragraph 24. The process of any preceding paragraph wherein step c) and/or c') is carried out in the presence of DMSO.

Paragraph 25. The process of any one of paragraphs 1-23 wherein step c) and/or c') is carried out in the presence of DMF.

Paragraph 26. The process of any preceding paragraph wherein steps c) and/or c') take place in less than 30 hours or less than 20 hours.

Paragraph 27. The process of any preceding paragraph wherein steps c) and/or c') take place in between 15 mins and 30 hours, or between 10 hours and 20 hours.

Paragraph 28. The process of any preceding paragraph wherein step c) and/or c') do not result in the production of cyanide ions.

Paragraph 29. The process of any preceding paragraph wherein the antigen and the carrier protein are mixed together before step b) and/or before step a').

Paragraph 30. The process of any preceding paragraph wherein the antigen and the carrier protein are lyophilised before step b).

Paragraph 31. The process of any preceding paragraph wherein the antigen and the carrier protein are lyophilised after step a).

Paragraph 32. The process of any one of paragraphs 30 or 31 wherein the antigen and the carrier protein are lyophilised in the presence of a non-reducing sugar.

Paragraph 33. The process of paragraph 32 wherein the non-reducing sugar is selected from the group consisting of sucrose, lactose, trehalose, raffinose, stachyose, melezitose, dextran, mannitol, lactitol and palatinit.

Paragraph 34. The process of any preceding paragraph wherein between 0.5 and 3, between 0.5 and 10 or between 8 and 12 molar equivalent of reducing agent is used in step c) and/or c').

Paragraph 35. The process of paragraph 34 wherein between 0.5 and 0.8 molar equivalent of reducing agent is used in step c) and/or c').

Paragraph 36. The process of any one of paragraphs 34 or 35 wherein between 2 and 3 molar equivalent of reducing agent is used in step c) and/or c').

Paragraph 37. The process of any preceding paragraph wherein the ratio of carrier protein:antigen before step c) and/or c') is between 0.4:1 and 2:1 or between 0.4/1 and 2.5/1.

Paragraph 38. The process of paragraph 37 wherein the ratio of carrier protein:antigen before step c) and/or c') is between 1:1 and 2:1.

Paragraph 39. The process of any preceding paragraph wherein the ratio of carrier protein:antigen after step c) and/or c') is between 0.8:1 and 3.5:1.

Paragraph 40. The process of paragraph 39 wherein the ratio of carrier protein:antigen after step c) and/or c') is between 1.3:1 and 2.7:1.

Paragraph 41. The process of paragraph 39 wherein the ratio of carrier protein:antigen after step c) and/or c') is between 1:1 and 1.5:1.

Paragraph 42. The process of any preceding paragraph wherein any unreacted carbonyl groups are capped by reaction with sodium borohydride ($NaBH_4$).

Paragraph 43. The process of paragraph 42 wherein between 1-10 molar equivalents of sodium borohydride are used.

Paragraph 44. The process of any one of paragraphs 42-43 wherein the product of step c) or c') is reacted with sodium borohydride for 15 mins-15 hrs.

Paragraph 45. The process of paragraph 44 wherein step a) comprises reacting the antigen with periodate.

Paragraph 46. The process of paragraph 45 wherein step a) comprises reacting the antigen with 0.001-0.7 molar equivalents of periodate.

Paragraph 47. The process of any preceding paragraph wherein step a) occurs in a buffer which does not contain an amine group.

Paragraph 48. The process of paragraph 47 wherein the buffer is selected from the group consisting of phosphate buffer, maleate buffer, borate buffer, acetate buffer, carbonate buffer and citrate buffer.

Paragraph 49. The process of paragraph 48 wherein the buffer is phosphate buffer.

Paragraph 50. The process of any one of paragraphs 47-49 wherein the buffer has a concentration between 1-50 mM, 1-25 mM, 1-10 mM, 5-15 mM, 8-12 mM, or 10-50 mM or around 10 mM.

Paragraph 51. The process of any one of any preceding paragraph wherein the pH during step a) is pH 3.0-8.0, pH 5.0-7.0, or pH 5.5-6.5 or around pH 6.0.

Paragraph 52. The process of any preceding paragraph wherein step a) is carried out in the dark.

Paragraph 53. The process of any one of paragraphs 6-14 or 16-52 wherein the antigen is either a native bacterial saccharide or is a bacterial saccharide that has been reduced in size by a factor of no more than ×20 (for instance by microfluidization).

Paragraph 54. The process of paragraph 53 wherein the antigen is microfluidised before step a).

Paragraph 55. The process of any preceding paragraph wherein the average molecular weight of the antigen is between 1-1100 kDa, 100-470 kDa, 200-300 kDa, 600-1100 kDa or 800-1000 kDa after step a).

Paragraph 56. The process of paragraph 55 wherein the average molecular weight of the antigen is between 100-470 kDa or 200-300 kDa after step a).

Paragraph 57. The process of paragraph 55 wherein the average molecular weight of the antigen is between 1 and 50 kDa or between 5 and 10 kDa after step a).

Paragraph 58. The process of any preceding paragraph comprising a further step e) of purifying the conjugated antigen.

Paragraph 59. The process of paragraph 58 wherein step e) comprises purifying the conjugated antigen using diafiltration.

Paragraph 60. The process of any one of paragraphs 58-59 wherein step e) comprises purifying the conjugated antigen using ion exchange chromatography.

Paragraph 61. The process of any one of paragraphs 58-60 wherein step e) further comprises gel permeation chromatography.

Paragraph 62. The process of any preceding paragraph comprising a further step f) wherein the conjugated antigen is sterile filtered.

Paragraph 63. The process of any preceding paragraph containing a further step of mixing the conjugated antigen with further antigens.

Paragraph 64. The process of paragraph 63 wherein the further antigens comprises at least 7, 8, 9, 10, 11, 12, 13, 14, 15, 16, 17, 18, 19 or 20 *S. pneumoniae* saccharides selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F.

Paragraph 65. The process of any one of paragraphs 63-64 wherein the further antigens comprise *S. pneumoniae* saccharides 4, 9V, 14, 18C, and 19F.

Paragraph 66. The process of any one of paragraphs 63-65 wherein the further antigens comprise *S. pneumoniae* saccharide 19A.

Paragraph 67. The process of any one of paragraphs 63-66 wherein the further antigens comprise *S. pneumoniae* saccharide 6A.

Paragraph 68. The process of any one of paragraphs 63-67 wherein the further antigens comprise *S. pneumoniae* saccharide 1.

Paragraph 69. The process of any one of paragraphs 63-68 wherein the further antigens comprise *S. pneumoniae* saccharide 5.

Paragraph 70. The process of any one of paragraphs 63-69 wherein the further antigens comprise *S. pneumoniae* saccharide 7F.

Paragraph 71. The process of any one of paragraphs 63-70 wherein the further antigens comprise *S. pneumoniae* saccharide 3.

Paragraph 72. The process of any one of paragraphs 63-71 wherein the further antigens comprise *S. pneumoniae* saccharide 23F.

Paragraph 73. The process of any one of paragraphs 63-72 wherein the further antigens comprise *S. pneumoniae* saccharide 6B.

Paragraph 74. The process of any one of paragraphs 63-73 wherein the further antigens comprise *S. pneumoniae* saccharide 6A.

Paragraph 75. The process of any one of paragraphs 63-74 wherein the further antigens comprise *S. pneumoniae* saccharide 33F.

Paragraph 76. The process of any one of paragraphs 63-75 wherein the further antigens comprise one or more *S. pneumoniae* proteins selected from the group consisting of the Poly Histidine Triad family (PhtX), Choline Binding Protein family (CbpX), CbpX truncates, LytX family, LytX truncates, CbpX truncate-LytX truncate chimeric proteins (or fusions), pneumolysin (Ply), PspA, PsaA, Sp128, Sp101, Sp130, Sp125 and Sp133.

Paragraph 77. The process of any one of paragraphs 63-76 wherein the further antigens comprise Diphtheria Toxoid (DT), Tetanus Toxoid (TT), and either killed whole-cell *Bordetella pertussis* (Pw), or two or more acellular pertussis components (Pa).

Paragraph 78. The process of any one of paragraphs 63-77 wherein the further antigens comprise Hepatitis B surface antigen (HepB)

Paragraph 79. The process of any one of paragraphs 63-78 wherein the further antigens comprise one or more conjugates of a carrier protein and a capsular polysaccharide of a bacterium selected from the group consisting of *N. meningitidis* type A (MenA), *N. meningitidis* type C (MenC), *N. meningitidis* type W (MenW) and *N. meningitidis* type Y (MenY).

Paragraph 80. The process of any preceding paragraph wherein the conjugated antigen is mixed with an adjuvant.

Paragraph 81. The process of paragraph 80 wherein the adjuvant is an aluminium salt.

Paragraph 82. An immunogenic composition comprising the conjugated antigen mixed with a pharmaceutically acceptable excipient.

Paragraph 83. An immunogenic composition obtainable by the process of any one of paragraphs 1-82.

Paragraph 84. An immunogenic composition obtained by the process of any one of paragraphs 1-82.

Paragraph 85. The immunogenic composition of any one of paragraphs 82-84 wherein the pharmaceutical excipient does not comprise sodium chloride.

Paragraph 86. The immunogenic composition of any one of paragraphs 82-85 wherein the immunogenic composition comprises maleate buffer.

Paragraph 87. The immunogenic composition of any one of paragraphs 82-86 further comprising an adjuvant.

Paragraph 88. The immunogenic composition of paragraph 87 wherein the adjuvant is an aluminium salt.

Paragraph 89. A vaccine comprising the immunogenic composition of paragraphs 82-88.

Paragraph 90. The immunogenic composition of any one of paragraphs 82-88 or the vaccine of paragraph 89 for use in the treatment or prevention of disease for example bacterial disease.

Paragraph 91. The immunogenic composition of any one of paragraphs 82-88 or the vaccine of paragraph 89 for use in the treatment or prevention of a disease selected from the group consisting of bacterial meningitis, pneumococcal disease, *Haemophilus influenzae* disease, meningococcal disease, staphylococcal disease, enterococcal disease and *Salmonella*.

Paragraph 92. A use of the immunogenic composition of any one of paragraphs 82-88 or the vaccine of paragraph 89 in the prevention or treatment of disease for example bacterial disease.

Paragraph 93. A use of the immunogenic composition of any one of paragraphs 82-88 or the vaccine of paragraph 89 in the prevention or treatment of a disease selected from the group consisting of bacterial meningitis, pneumococcal disease, *Haemophilus influenzae* disease, meningococcal disease, staphylococcal disease, enterococcal disease and *Salmonella*.

Paragraph 94. A use of the immunogenic composition of any one of paragraphs 82-88 or the vaccine of paragraph 89 in the manufacture of a medicament for the prevention or treatment of disease for example bacterial disease.

Paragraph 95. A use of the immunogenic composition of any one of paragraphs 82-88 or the vaccine of paragraph 89 in the manufacture of a medicament for the prevention or treatment of a disease selected from the group consisting of bacterial meningitis, pneumococcal disease, *Haemophilus influenzae* disease, meningococcal disease, staphylococcal disease, enterococcal disease and *Salmonella*.

Paragraph 96. A method of preventing or treating infection for example bacterial infection comprising administering the immunogenic composition of paragraphs 82-88 or the vaccine of paragraph 89 to a patient.

Paragraph 97. A method of preventing or treating a disease selected from the group consisting of bacterial meningitis, pneumococcal disease, *Haemophilus influenzae* disease, meningococcal disease, staphylococcal disease, enterococcal disease and *Salmonella* comprising administering the immunogenic composition of paragraphs 82-88 or the vaccine of paragraph 89 to a patient.

EXAMPLES

Example 1

Oxidation of 23F and 6B Using Periodate

Polysaccharides (PS) 23F or 6B were dissolved in 100 mM $KH_2PO_4$ (pH 7.4), 10 mM $KH_2PO_4$ or WFI, to form solutions of 2 mg PS/ml. The solution was incubated for 2 hours under agitation at room temperature. After this time the pH was adjusted to pH 6.0 with 1NHCl. Periodate was added as a powder or in liquid form (10 mg/ml in WFI) in various amounts to achieve a range of molar ratios (table 1). The solutions were incubated for 17 hours at room temperature (20-25° C.), after which time the samples were dialyzed or diafiltered against WFI.

High performance gel filtration chromatography coupled with refractive index and multiangle laser lights scattering (MALLS-) detectors was used to measure the molecular weight. Size exclusion media (TSK5000PWXL-Tosoh) was used to profile the molecular size distribution of the polysaccharide (elution 0.5 ml/min in NaCl 0.2M-NaN3 0.02%).

Table 1 and FIG. 1 describe the results of these experiments. Table 1 refers to samples labelled 23F and 23FATCC. The samples labelled 23F were 23F samples produced in GSK, whereas the samples labelled 23FATCC were carried out using a cell line obtained from ATCC (American Type Culture Collection). These results demonstrate that for the 23F saccharide substantial sizing occurs on oxidation using high molar equivalents of periodate in 100 mM phosphate buffer. This sizing effect can be reduced by reducing the concentration of phosphate buffer or the molar equivalents of periodate used.

TABLE 1

| | 23F | | | | 6B | | |
|---|---|---|---|---|---|---|---|
| Sample | molar equivalent of periodate | Buffer | Size (KDa) | Sample | molar equivalent of periodate | buffer | Size (KDa) |
| 23F | 0 | Water | 861 | 6B | 0 | 10 mM phosphate | 1022 |
| 23F | 0 | 10 mM phosphate | 847 | 6B | 0.1 | 10 mM phosphate | 975 |
| 23F | 0 | 100 mM phosphate | 860 | 6B | 0.2 | 10 mM phosphate | 990 |
| 23F ATCC | 0 | 100 mM phosphate | 1655 | 6B | 0.3 | 10 mM phosphate | 961 |
| 23F | 1 | 100 mM phosphate | <1 | 6B | 0.75 | 10 mM phosphate | 868 |
| 23F | 1 | Water | 36 | | | | |
| 23F | 1.2 | 100 mM phosphate | <1 | | | | |
| 23FATCC | 1 | 100 mM phosphate | 2 | | | | |
| 23FATCC | 0.125 | 100 mM phosphate | 39 | | | | |
| 23F | 0.1 | 10 mM phosphate | 466.9 | | | | |
| 23F | 0.15 | 10 mM phosphate | 398.5 | | | | |
| 23F | 0.2 | 10 mM phosphate | 336 | | | | |
| 23F | 0.5 | 10 mM phosphate | 179.1 | | | | |

Example 2

Conjugation of 23F to CRM197 Using Reductive Amination and CDAP Chemistry

Reductive Amination 1 g of PS23F was dissolved in 500 ml of 10 mM $KH_2PO_4$, pH 7.15. This solution was incubated at room temperature for two hours. The pH was adjusted to 6.0 with 1M HCl. 111 mg of periodate ($NaIO_4$, 0.4 molar equivalents of periodate) was added to the PS23F solution, and the solution was incubated for 17 hours in the dark at room temperature to oxidise PS23F. The solution was then diafiltered against WFI (cut off 100 kDa).

The activated PS23F was lyophilised with the CRM197 protein (at a CRM/PS ratio (w/w): 0.625) in the presence of a stabilising agent.

900 mg of the lyophilised PS23F/CRM197 mixture was solubilised by addition of 350 ml of DMSO solvent and incubating for 2 hours at room temperature. To reduce the PS23F/CRM197 mixture 1 molar equivalent of $NaBH_3CN$ was added (735 µl of a solution of 100 mg/ml in WFI). The solution was incubated for a further 40 hours room temperature (15° C.-25° C.) under agitation. After this time 2 molar equivalents of $NaBH_4$ (100 mg/ml in WFI) were added and the solution incubated for 4 hours at room temperature. 2200 ml of 150 mM NaCl were added before diafiltration (cut-off 100 kDa) and purification by DEAE. The fractions of interest were pooled and filtered through a 0.22 µm filter.

CDAP 200 mg of microfluidized PS23F were dissolved in WFI until a concentration of 10 mg/ml was obtained. NaCl was added to this solution at a final concentration of 2M.

Sufficient CDAP solution (100 mg/ml freshly prepared in 5/50 v/v acetonitrile/WFI) was added to reach a CDAP/PS ratio of 0.75/1 (w/w)

After 90 seconds, the pH was raised to pH 9.5 by addition of 0.1N NaOH. 3 minutes later sufficient CRM197 (10 mg/ml in 0.15M NaCl) was added to reach a ratio of 1.5 (CRM197:PS (w/w)), the pH was maintained at pH 9.5. This solution was incubated for 1 hour at pH 9.5.

After this coupling step, 10 ml of 2M glycine solution was added to the mixture and the pH was adjusted to pH 9.0 (the quenching pH). The solution was stirred for 30 minutes at room temperature. The conjugate was purified using a 5 µm filter followed by Sephacryl S400HR which removes small molecules and unconjugated polysaccharides and protein. Elution was achieved using 150 mM NaCl. The fractions of interest were pooled and filtered on 0.22 µm membrane. The resulting conjugate had a final CRM197/PS ratio (w/w) of 1.35/1.

Example 3

Immunogenicity of 23F-CRM197 Conjugates Made by Reductive Amination and CDAP Chemistry Conjugates were made using the methods described in example 2. Female guinea pigs were immunized intramuscularly three times (at days 0, 14 and 28) with 0.25 µg of the PS23F-CRM197 conjugates. Animals were bled on day 42 and the antibody response directed against PS23F was measured by ELISA and OPA.

ELISA

Microplates were coated with purified pneumococcal polysaccharide in PBS buffer. The plates were washed four times with 0.9% NaCl and 0.05% Tween 20. Sera were incubated for 1 hour at 37° C. with CPS (V/V) in PBS 0.05% Tween 20. Sera were added to the microwells and serially diluted (two-fold dilution step) in PBS-0.05% Tween. The plates were incubated under agitation for 30 minutes at room temperature. The plates were washed as above and an anti-guinea pig IgG antibodies peroxydase conjugate was added, the plates were then incubated for 30 minutes at RT. After washing, the substrate (4 mg of OPDA in 10 ml of citrate 0.1M pH 4.5 and 5 µl of $H_2O_2$) was added to each well for 15 minutes. The reaction was stopped by addition of HCl 1N. Absorbance was read at 490-620 nm using a spectrophotometer. The colour developed is directly proportional to the amount of antibody present in the serum. The level of anti-PS IgG present in the sera is determined by comparison to the reference curve serum added on each plate and expressed in µg/ml.

Results were analysed statistically after assuming homogeneity of variance (checked by Cochrans's C test) and normality (checked using the Shapiro-Wilk test). All statistics were carried out using Anova (Tukey-HSD) on log transformation concentration IgG.

Opsonophagocytosis

Serum samples were heated for 45 min at 56° C. to inactivate any remaining endogenous complement. Twenty-five microlitre aliquots of each 1:2 diluted serum sample were serially diluted (two fold) in 25 µl OPA buffer (HBSS—14.4% inactivated FBS) per well of a 96-well round bottom microtitre plate. Subsequently, 25 µl of a mixture of activated HL-60 cells (1×107 cells/ml), freshly thawed pneumococcal working seed and freshly thawed baby rabbit complement in an e.g. 4/2/1 ratio (v/v/v) was added to the diluted sera to yield a final volume of 50 µl. The assay plate was incubated for 2 h at 37° C. with orbital shaking (210 rpm) to promote the phagocytic process. The reaction was stopped by laying the microplate on ice for at least 1 min. A 20 µl aliquot of each well of the plate was then transferred into the corresponding well of a 96-well flat bottom microplate and 50 µl of Todd—Hewitt Broth—0.9% agar was added to each well. After overnight incubation at 37° C. and 5% CO2, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Results were analysed statistically after assuming homogeneity of variance (checked by Cochrans's C test) and normality (checked using the Shapiro-Wilk test). All statistics were performed by Anova (Tukey-HSD) on log transformation concentration IgG for ELISA and Kruskal-Wallis on log dilution for OPA.

A significantly higher antibody response was induced in the guinea pigs after immunisation with PS23F-CRM197 conjugated by reductive amination than PS23F-CRM197 conjugated by CDAP chemistry as seen in FIG. 2.

TABLE 2

| Assay | 23F-CRM197 made by reductive amination | 23F-CRM197 made by CDAP |
|---|---|---|
| ELISA Titer (µg/ml) | 213.3 | 40.5 |
| OPA (50% killing) | 9232 | 591 |

Example 4

A Further Example of Reductive Amination of 23F

23F-CRM-RA-116

150 mg of native PS23F (PS23FP114) were dissolved at a concentration of 2 mg/ml in 10 mM phosphate buffer (pH 7.2) for 4 hours. After dissolution, pH was adjusted to pH 6.0 with 1N HCl. Then 0.4 molar equivalent of periodate ($NaIO_4$) was added to the PS solution and incubated for 17 hrs in the dark at 25° C. The solution was then diafiltered (cut off 30 kDa) against WFI and the oxidised PS was filtered on 0.22 µm membrane.

50 mg of oxidised PS and 75 mg of CRM197 were lyophilized together (CRM/PS ratio (w/w): 1.5/1) with a stabilising agent. Lyophilized PS+CRM197 were solubilised with 20 ml of DMSO for 2 hrs at room temperature (15-25° C.). 1 molar equivalent of Sodium triacetoxyborohydride was then added (13.7 mg) and after 17 hrs under agitation, 2 molar equivalent of $NaBH_4$ (100 mg/ml in 0.1M NaOH) were added followed by an incubation at room temperature for 30 minutes. The solution was diluted 5× by addition of WFI followed by a diafiltration (cut-off 30 kDa) against 10 mM phosphate buffer, 150 mM NaCl pH 7.2. The conjugate was then loaded onto DEAE resin and eluted in 10 mM phosphate buffer, 500 mM NaCl pH 7.2. The conjugate was finally filtered on 0.22 µm. The resulting conjugate has a final CRM/PS ratio (w/w) of 2.3/1.

For further conjugates, a second diafiltration step was added after DEAE column in order to change the buffer (150 mM NaCl as final buffer).

Example 5

Conjugation of 6B to CRM197 Using Reductive Amination (with Different Protein:Saccharide Ratios and Different Sized Microfluidised 6B Saccharides) and CDAP Chemistry

6B-CRM-RA-122

200 mg of microfluidized PS6B (84 kDa, 11.7 mg/ml) were diluted at 2 mg/ml in 10 mM phosphate buffer (pH 7.2). pH was adjusted to pH 6.0 with 1N HCl. Then 0.1 molar equivalent of periodate (Na $IO_4$) was added to the PS solution and incubated for 17 hrs in the dark at room temperature. The solution is then diafiltered (cut off 30 kDa) against WFI. 50 mg of PS and 30 mg of CRM197 were lyophilized together (CRM/PS ratio (w/w): 0.6/1) with a stabilising agent. Lyophilized PS+CRM197 were solubilised with 20 ml of DMSO for 3 hrs at room temperature. Then 2.5 molar equivalents of sodium triacetoxyborohydride were added (38.7 mg) and after 16 hrs under agitation, 2 molar equivalents of $NaBH_4$ (100 mg/ml in 0.1M NaOH) were added followed by an incubation at room temperature for 30 minutes. The solution was diluted 4× by addition of WFI followed by a diafiltration (cut-off 100 kDa). The conjugate was then filtered on 0.22 µm. The resulting conjugate has a final CRM/PS ratio (w/w) of 1.1/1.

6B-CRM-RA-123:

Microfluidized PS6B (84 kDa) was conjugated to CRM197 as described for 6B-CRM-RA-122 except the freeze-drying step was carried out using an initial CRM197/PS ratio (w/w) of 2/1 and 33 ml of DMSO was used for the dissolution in DMSO step (instead of 20 ml). The resulting conjugate had a final CRM/PS ratio (w/w) of 3.0/1.

6B-CRM-RA-124:

200 mg of microfluidized PS6B (350 kDa,) were diluted to 2 mg/ml in 10 mM phosphate buffer (pH 7.2). pH was adjusted to pH 6.0 with 1N HCl. Then 0.1 molar equivalent of periodate ($NaIO_4$) was added to the PS solution and incubated for 17 hrs in the dark at room temperature. The solution was then diafiltered (cut off 100 kDa) against WFI. 50 mg of PS and 60 mg of CRM197 were lyophilized together (CRM/PS ratio (w/w): 1.2/1) with a stabilising agent. Lyophilized PS+CRM197 were solubilised with 20 ml of DMSO for 5 hrs at room temperature. 2.5 molar equivalents of sodium triacetoxyborohydride were then added (38.7 mg) and after 16 hrs under agitation, 2 molar equivalents of $NaBH_4$ (100 mg/ml in 0.1M NaOH) were added followed by incubation for 30 min at room temperature. The solution was diluted 4× by addition of WFI followed by a diafiltration (cut-off 100 kDa). The conjugate was then filtered on 0.22 µm. The resulting conjugate has a final CRM/PS ratio (w/w) of 1.6/1.

6B-CRM-RA-125:

Microfluidized PS6B (350 kDa) was conjugated to CRM197 as described for 6B-CRM-RA-124 except the freeze-drying step was carried out using an initial CRM197/PS ratio (w/w) of 2/1 and the dissolution in DMSO was carried out using 33 ml (instead of 20 ml). The resulting conjugate had a final CRM/PS ratio (w/w) of 2.9/1.

6B-CRM-003:

50 mg of microfluidized PS6B were diluted at 10 mg/ml in WFI. NaCl in solid form was added to reach a final concentration of 2M. CDAP solution (100 mg/ml freshly prepared in 50/50 v/v acetonitrile/WFI) was added to reach the appropriate CDAP/PS ratio (1.5 mg/mg PS). After 1.5 minutes, the pH was raised to the activation pH 9.5 by addition of 0.1N NaOH and was stabilised at this pH until addition of CRM197. After 3 minutes, CRM197 (10 mg/ml in 0.15 M NaCl) was added to reach a ratio CRM197/PS (w/w) of 2; the pH was maintained at the coupling pH 9.5. The solution was left for 2 hrs under pH regulation.

After the coupling step, 2.5 ml of 2M glycine solution were added to the mixture. The pH was adjusted to the quenching pH (pH 9.0). The solution was stirred for 30 min at room temperature. Then the conjugate was filtered using a 5 µm filter and injected on Sephacryl S400HR column. Elution was carried out in 150 mM NaCl. Interesting fractions were pooled and filtered on 0.22 µm membrane. The resulting conjugate had a final CRM197/PS ratio (w/w) of 1.5/1.

6B-CRM-RA-144

1 g of microfluidized PS6B (245 kDa,) was diluted to 2 mg/ml in 10 mM phosphate buffer (pH 7.2). The pH was adjusted to pH 6.0 with 1N HCl. 0.1 molar equivalent of periodate ($NaIO_4$) was then added to the PS solution and incubated for 18 hrs in the dark at room temperature. The solution was then diafiltered against WFI (Cut-off 100 kDa). 200 mg of oxidized PS and 240 mg of CRM197 were lyophilized together (CRM/PS ratio (w/w): 1.2/1) with a stabilising agent. Lyophilized PS+CRM197 were solubilised with 80 ml of DMSO for 6 hrs at 25° C. Then 2.5 molar equivalents of sodium triacetoxyborohydride) were added (154.9 mg) and after 16 hrs under agitation at 25° C., 2 molar equivalents of $NaBH_4$ (100 mg/ml in 0.1M NaOH) were added and incubated for 30 min. The solution was diluted 5× in WFI and after 30 min was diafiltered 10× with 150 mM NaCl and then 5× with $PO_4$ ($K/K_2$) 10 mM pH7.2/150 mM NaCl (Cut-off100 kDa). Then the retentate was loaded onto a DEAE column. The column was washed with $PO_4$ ($K/K_2$) 10 mM pH7.2/NaCl 150 mM buffer. The conjugate was eluted with $PO_4$ ($K/K_2$) 10 mM pH7.2/NaCl 500 mM buffer. The eluate was concentrated and diafiltered with 5 volumes of 150 mM NaCl and then filtered on 0.22 µm filter. The resulting conjugate has a final CRM/PS ratio (w/w) of 1.6/1.

Example 6

Immunogenicity of 6B-CRM197 Conjugates Made by Reductive Amination and CDAP Chemistry Groups of 40 female Balb/c mice (4 weeks-old) were immunized intramuscularly three times at days 0, 14 and 28 with 0.1 µg of PS6B conjugates produced by reductive amination or CDAP chemistry formulated on $AlPO_4$. PS6B-PD was used as benchmark. Mice were bled on day 42 and the antibody response directed against each antigen was measured by ELISA and OPA.

Groups of 20 female guinea pig (150 gr from Hartley) were immunized intramuscularly three times at days 0, 14 and 28 with 0.25 µg of PS6B conjugates produced by reductive amination or CDAP chemistry adjuvanted with $AlPO_4$. PS6B-PD was used as benchmark. Guinea pigs were bled on day 42 and the antibody response directed against each antigen was measured by ELISA and OPA.

Mouse and Guinea Pig OPA

Serum samples were heated for 45 min at 56° C. to inactivate any remaining endogenous complement. Twenty-five microlitre aliquots of each 1:2 diluted serum sample was two-fold serially diluted in 25 µl OPA buffer (HBSS—14.4% inactivated FBS) per well of a 96-well round bottom microtitre plate. Subsequently, 25 µl of a mixture of activated HL-60 cells ($1 \times 10^7$ cells/rya freshly thawed pneumococcal working seed and freshly thawed baby rabbit complement in an e.g. 4/2/1 ratio (v/v/v) were added to the diluted sera to yield a final volume of 50 µl. The assay plate was incubated for 2 h at 37° C. with orbital shaking (210 rpm) to promote the phagocytic process. The reaction was stopped by laying the microplate on ice for at least 1 min. A 20 µl aliquot of each well of the plate was then transferred into the corresponding well of a 96-well flat bottom microplate and 50 µl of Todd-Hewitt Broth—0.9% agar was added to each well. After overnight incubation at 37° C. and 5% $CO_2$, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Table 3 describes the GMC levels obtained by immunisation of balb/c mice with the conjugates made using the methods of example 4.

TABLE 3

| Subject/Result | G1 | G2 | G3 | G4 | G5 | G6 |
|---|---|---|---|---|---|---|
| | PS06B-CRM122 (R: 1/1, PS 84) | PS06B-CRM123 (R: 3/1, PS 84 kDa) | PS06B-CRM124 (R: 1.5/1, PS 350 kDa) | PS06B-CRM125 (R: 2.9/1, PS 350 kDa) | PS06B-CRM003 (CDAP) | PS06B-PD |
| GMC (UG-ML) | 0.83 | 0.37 | 1.18 | 0.64 | 0.31 | 0.10 |
| Responders (%) | 31/40 | 26/40 | 33/40 | 29/40 | 29/40 | 15/40 |

Figure 3:
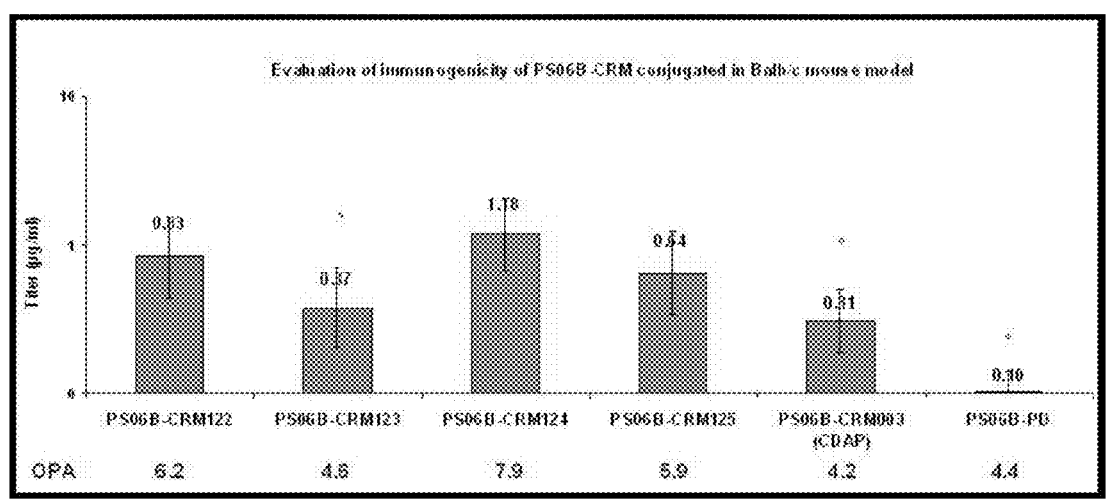
FIG. 3. Evaluation of the immunogenicity of PS06B-CRM conjugated using the conjugation methods described in example 4 in a Balb/c mouse model.

The immunogenicity of these conjugates in balb/c mice is described in FIG. 3. Together FIG. 3, and table 3 demonstrate that in the mouse model the conjugates produced by reductive amination were comparable with those produced using CDAP chemistry. In particular FIG. 3 demonstrates that the immunogenicities of the conjugates produced using reductive amination was higher than the immunogenicity of the conjugate made using CDAP chemistry.

Table 4 describes the GMC levels obtained by immunisation of guinea pigs with the conjugates made using the methods of example 4.

(100 mg/ml in 0.1M NaOH) were added followed by an incubation of 30 min at room temperature. The solution was diluted 3× by addition of WFI followed by a diafiltration step (5 volumes of WFI followed by 5 volumes of 10 mM acetate buffer 150 mM NaCl pH 6.2, 100 kDa MWCO). The sample was then loaded on Sephacryl S300HR resin. Elution was carried out in 10 mM acetate buffer using 150 mM NaCl (pH 6.2). Interesting fractions were pooled and filtered on a 0.22 μm filter. The resulting conjugates had a final TT/PS ratio (w/w) of 2.1/1.

TABLE 4

| Subject/Result | G1 | G2 | G3 | G4 | G5 | G6 |
|---|---|---|---|---|---|---|
| | PS06B-CRM122 (R: 1/1, PS 84 kDa) | PS06B-CRM123 (R: 3/1, PS84 kDa) | PS06B-CRM124 (R: 1.5/1, PS0350 kDa) | PS06B-CRM126 (R: 2.9/1, PS 350 kDa) | PS06B-CRM003 (CDAP) | PS06B-PD |
| GMC (UG-ML) | 3.51 | 7.70 | 2.84 | 19.93 | 3.70 | 1.55 |
| Responders (%) | 20/20 | 20/20 | 20/20 | 20/20 | 20/20 | 20/20 |

Figure 4:
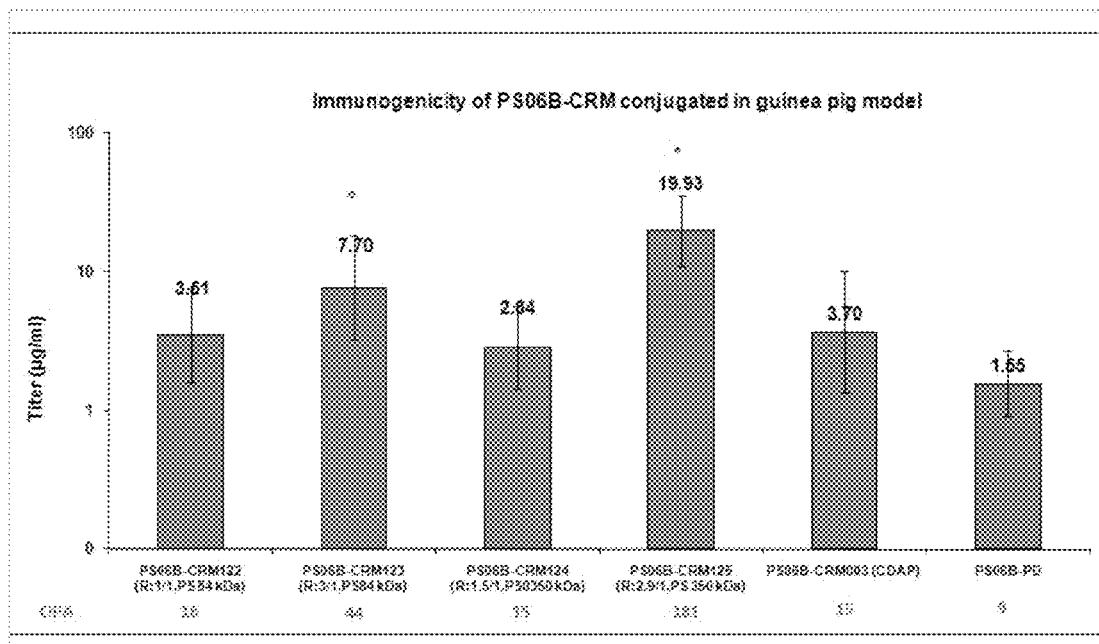
FIG. 4. Evaluation of the immunogenicity of PS06B-CRM conjugated using the conjugation methods described in example 4 in a guinea pig model.

The immunogenicity of these conjugates in guinea pigs is described in FIG. 4. Similar to the experiments carried out in the mouse model, the results in table 4 and FIG. 4 show that the conjugates produced by reductive amination were comparable with those produced using CDAP chemistry, in particular PS06B-CRM125 demonstrated significantly higher GMC levels and immunogenicities than the conjugate produced using CDAP.

Example 7

Conjugation of Hib to Tetanus Toxoid Using Reductive Amination

Hib-104-LS080

2.9 g of PS (orcinol dosage, AHIBCPA007 lot) were dissolved in 260 ml of 10 mM phosphate buffer (Na/K$_2$) pH 6.2 for 4 h30 at room temperature and then overnight at +4° C. After 4 hours dissolution, PS was diluted at 10 mg/ml with phosphate buffer and then oxidised in the dark with 0.07 molar equivalent of NaIO$_4$ during 60 minutes. Oxidised PS was diafiltered (Cut-off2 kDa) against 3.5 volumes of phosphate buffer and then filtered on a 0.22 μm filter. The number of repeating units obtained after oxidation was estimated by $^1$H-NMR and was found to be around 21.

Hib-TT-LS210, 212 and 213

200 mg of oxidised PS (14.56 mg/ml) were mixed with 300 mg of TT (31.18 mg/ml, TT/PS ratio (w/w): 1.5/1) and diluted to 4 mg/ml with 36.64 ml of 10 mM phosphate buffer (Na/K$_2$) pH 6.2. The solution was lyophilized with a stabilising agent. Lyophilized PS+TT was solubilised with 20 ml of DMSO for 6 hrs at 25° C. Then 10 molar equivalentseq of sodium triacetoxyborohydride were added (38.7 mg) and after 16 hrs under agitation, 2 molar equivalents of NaBH$_4$

The invention claimed is:

1. A process for preparing an immunogenic composition comprising conjugating an antigen to a carrier protein wherein conjugating comprises
    a) activating the antigen to form an activated antigen;
    b) reacting the activated antigen and a carrier protein to form an imine group linking the activated antigen to the carrier protein;
    c) reductive amination of the imine group in a solution consisting essentially of a reducing agent in dimethylsulphoxide (DMSO) or dimethylformamide (DMF), wherein the reducing agent consists of sodium triacetoxyborohydride, to form a conjugated antigen; and
    c") capping unreacted carbonyl groups using sodium borohydride in a solution consisting essentially of DMSO or DMF;
    or
    a) activating the antigen to form an activated antigen;
    b') reacting the activated antigen and a liner to form an imine group linking the activated antigen to the linker;
    c') reductive amination of the imine group in a solution consisting essentially of a reducing agent in dimethylsulphoxide (DMSO) or dimethylformamide (DMF), wherein the reducing agent consists of sodium triacetoxyborohydride, to form an antigen-linker;
    c") capping unreacted carbonyl groups using sodium borohydride in a solution consisting essentially of DMSO or DMF;
    d) reacting the antigen-linker with a carrier protein to form a conjugated antigen; and
    e) mixing the conjugated antigen with a pharmaceutically acceptable excipient to form the immunogenic composition,
    wherein the antigen is a bacterial capsular saccharide from a *Streptococcus pneumonia* serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F, and 33F, wherein the average molecular weight of the bacterial saccharide is between 20 kDa and 2000 kDa, and wherein step a) comprising reacting the antigen with periodate.

2. A process for preparing an immunogenic composition conjugating an antigen to a carrier protein wherein conjugating comprises
a) activating the antigen to form an activated antigen;
a') lyophilizing the activated antigen and a carrier protein followed by reconstitution in dimethylsulphoxide (DMSO) or dimethylformamide (DMF)
b) reacting the activated antigen and a carrier protein to form an imine group linking the activated antigen to the carrier protein;
c) reductive amination of the imine group in a solution consisting essentially of a reducing agent in dimethylsulphoxide (DMSO) or dimethylformamide (DMF), wherein the reducing agent consists of sodium triacetoxyborohydride, to form a conjugated antigen; and
c") capping unreacted carbonyl groups using sodium borohydride in a solution consisting essentially of DMSO or DMF;
or
a) activating the antigen to form an activated antigen;
a') lyophilizing the activated antigen and a linker followed by reconstitution in DMSO or DMF;
b') reacting the activated antigen and a linker to form an imine group linking the activated antigen to the carrier protein; and
c') reductive amination of the imine group in a solution consisting essentially of a reducing agent in dimethylsulphoxide (DMSO) or dimethylformamide (DMF), wherein the reducing agent consists of sodium triacetoxyborohydride, to form an antigen-linker;
c") capping unreacted carbonyl groups using sodium borohydride in a solution consisting essentially of DMSO or DMF;
d) reacting the antigen-linker with a carrier protein to form a conjugated antigen; and
e) mixing the conjugated antigen with a pharmaceutically acceptable excipient to form the immunogenic composition,
wherein the antigen is a bacterial capsular saccharide from a *S. pneumonia* serotype selected from the group consisting of 1, 2, 3, 4, 5, 6A, 7F, 8, 9N, 9V, 10A, 11A, 12F, 14, 15B, 17F, 18C, 19A, 19F, 20, 22F and 33F, wherein the average molecular weight of the bacterial saccharide is between 20 kDa and 2000 kDa, and wherein step a) comprises reacting the antigen with periodate.

3. The process of claim 1 wherein the bacterial saccharide is *Haemophilus influenzae* b (Hib) polysaccharide or oligosaccharide.

4. The process of claim 1 wherein the carrier protein is a protein selected from the group consisting of tetanus toxoid (TT), fragment C of TT, diphtheria toxoid, CRM197, pneumolysin, Protein D, PhtD, and PhtDE.

5. The process of claim 1 wherein the antigen and the carrier protein are lyophilised after step a).

6. The process of claim 5 wherein the antigen and the carrier protein are lyophilised in the presence of a non-reducing sugar.

7. The process of claim 1 wherein step a) comprises reacting the antigen with 0.0001-0.7 molar equivalents of periodate.

8. The process of claim 1 comprising a further step f) of mixing the conjugated antigen with further antigens.

9. The process of claim 8 wherein the further antigens comprise at least 7, 8, 9, 10, 11, 12, 13, 14, 15, 16, 17, 18, 19 or 20 *S. pneumoniae* saccharides.

10. The process of claim 1 wherein the conjugated antigen is mixed with an adjuvant optionally wherein the adjuvant is an aluminium salt.

11. The process of claim 1 wherein the bacterial capsular saccharide is *S. pneumonia* capsular saccharide 23F.

12. The process of claim 1 wherein the bacterial capsular saccharide is *S. pneumonia* capsular saccharide 6B.

* * * * *